(12) United States Patent
Sherman et al.

(10) Patent No.: US 12,721,754 B2
(45) Date of Patent: Sep. 1, 2026

(54) NON-ADHESIVE ELASTOMERIC ARTICLES

(71) Applicant: Solventum Intellectual Properties Company, Maplewood, MN (US)

(72) Inventors: Audrey A. Sherman, Woodbury, MN (US); Thomas R. Corrigan, St. Paul, MN (US); John J. Rogers, St. Paul, MN (US); Anne C.F. Gold, South St. Paul, MN (US); Silvia G.B. Guttmann, St. Paul, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 140 days.

(21) Appl. No.: 18/280,333

(22) PCT Filed: Mar. 3, 2022

(86) PCT No.: PCT/IB2022/051898
§ 371 (c)(1),
(2) Date: Sep. 5, 2023

(87) PCT Pub. No.: WO2022/189913
PCT Pub. Date: Sep. 15, 2022

(65) Prior Publication Data

US 2024/0041657 A1 Feb. 8, 2024

Related U.S. Application Data

(60) Provisional application No. 63/160,036, filed on Mar. 12, 2021.

(51) Int. Cl.

| | |
|---|---|
| ***A61F 13/01*** | (2024.01) |
| ***A61F 13/00*** | (2024.01) |
| ***A61F 13/08*** | (2006.01) |

(52) U.S. Cl.
CPC ........ *A61F 13/01046* (2024.01); *A61F 13/08* (2013.01); *A61F 2013/00119* (2013.01);
(Continued)

(58) Field of Classification Search
CPC .... A61F 13/00; A61F 13/01; A61F 13/00021; A61F 13/01021; A61F 13/01038;
(Continued)

(56) References Cited

U.S. PATENT DOCUMENTS

| | | | |
|---|---|---|---|
| 3,575,782 | A | 4/1971 | Hansen |
| 3,613,679 | A | 10/1971 | Bijou |

(Continued)

FOREIGN PATENT DOCUMENTS

| | | | |
|---|---|---|---|
| CN | 105671744 | A | 6/2016 |
| CN | 206044791 | U | 3/2017 |

(Continued)

OTHER PUBLICATIONS

International Search report for PCT International Application No. PCT/IB2022/051898, mailed on Jun. 13, 2022, 6 pages.

*Primary Examiner* — Caitlin A Carreiro

(57) ABSTRACT

Non-adhesive articles include an elastomeric layer, where the elastomeric layer has a plurality of cuts arrayed in a pattern. The cuts are gaps, but the gaps are not visible to the naked eye when the article is in an unstressed state, and in a stressed state, at least some of the cuts become gaps that are visible to the naked eye. The gaps are perforations in the elastomeric layer and are apertures through which one can view through the elastomeric layer. The perforations indicate the presence of stress in the article, and the elastomeric layer has a lower effective modulus of elasticity in at least one axis than an identical elastomeric layer without the plurality of cuts.

20 Claims, 9 Drawing Sheets

(52) U.S. Cl.
CPC ............... *A61F 2013/00251* (2013.01); *A61F 2013/0028* (2013.01)

(58) Field of Classification Search
CPC ................ A61F 13/01046; A61F 13/08; A61F 13/00004; A61F 13/00008; A61F 2013/00119; A61F 2013/00251; A61F 2013/0028; A61F 2013/00246; A61F 2013/00582
USPC ...................... 602/41, 47, 53, 58, 59, 75, 76
See application file for complete search history.

(56) References Cited

U.S. PATENT DOCUMENTS 4,984,585 A 1/1991 Austad
5,267,952 A 12/1993 Gardner
6,050,967 A 4/2000 Walker et al.
6,155,424 A 12/2000 Dubach
6,262,331 B1 7/2001 Nakahata et al.
2003/0114782 A1* 6/2003 Chiang ..................... B32B 3/30 602/61
2005/0228331 A1* 10/2005 Tseng ..................... A63B 71/14 602/58
2013/0251962 A1 9/2013 Reid, Jr.
2014/0276275 A1 9/2014 Stokes et al.
2014/0371650 A1 12/2014 Cobanoglu et al.
2015/0351969 A1 12/2015 Farrow et al.
2015/0374551 A1 12/2015 Dallafior
2016/0357034 A1 12/2016 Pothier
2017/0348155 A1 12/2017 Duesterhoft et al.
2017/0348156 A1 12/2017 Duesterhoft et al.
2018/0049482 A1 2/2018 Erkus et al.
2019/0262188 A1* 8/2019 Reid, Jr. ................ A61H 1/006
2019/0336351 A1 11/2019 Hitschmann et al.
2021/0401626 A1 12/2021 Bier

FOREIGN PATENT DOCUMENTS

CN 109419584 A 3/2019
DE 3640979 A1 8/1987
EP 0783405 B1 10/2001
GB 1374627 A 11/1974
GB 2543485 A 4/2017
RU 2643984 C1 2/2018
WO 2008152294 A1 12/2008
WO 2020094753 A1 5/2020
WO WO-2021130660 A1 * 7/2021 ........... B31D 5/0065

* cited by examiner

NON-ADHESIVE ELASTOMERIC ARTICLES

SUMMARY

Disclosed herein are non-adhesive articles and methods of using the non-adhesive articles. In many embodiments, the articles are elastomeric articles and are useful as compression articles for medical applications.

In some embodiments, the non-adhesive articles comprise an elastomeric layer wherein the elastomeric layer comprises a plurality of cuts, wherein the plurality of cuts is arrayed in a pattern, and wherein the cuts are gaps, but the gaps are not visible to the naked eye when the article is in an unstressed state, and in a stressed state, at least some of the cuts become gaps that are that are visible to the naked eye. The gaps are perforations in the elastomeric layer such that in a stressed state the perforations are apertures through which one can view through the elastomeric layer. The perforations indicate the presence of stress in the article, and the elastomeric layer has a lower effective modulus of elasticity in at least one axis than an identical elastomeric layer without the plurality of cuts.

Also disclosed herein are method of using non-adhesive articles, especially non-adhesive elastomeric articles. In some embodiments, the method comprises preparing a non-adhesive article, and wrapping the non-adhesive article upon itself such that the overlapping portions of the article self-adhere. The non-adhesive article is described above and comprises an elastomeric layer, wherein the elastomeric layer comprises a plurality of cuts, wherein the plurality of cuts is arrayed in a pattern, and wherein the cuts are gaps, but the gaps are not visible to the naked eye when the non-adhesive article is in an unstressed state, and in a stressed state, at least some of the cuts become gaps that are that are visible to the naked eye. The gaps are perforations in the elastomeric layer such that in a stressed state the perforations are apertures through which one can view through the non-adhesive article. The perforations indicate the presence of stress in the non-adhesive article, the elastomeric layer has a lower effective modulus of elasticity in at least one axis than an identical elastomeric layer without the plurality of cuts, and the non-adhesive article has increased breathability than an identical non-adhesive article without the plurality of cuts. The increased breathability is evidenced by an increased MVTR (Moisture Vapor Transmission Rate).

BRIEF DESCRIPTION OF THE DRAWINGS

The present application may be more completely understood in consideration of the following detailed description of various embodiments of the disclosure in connection with the accompanying drawings.

Figure 1A:
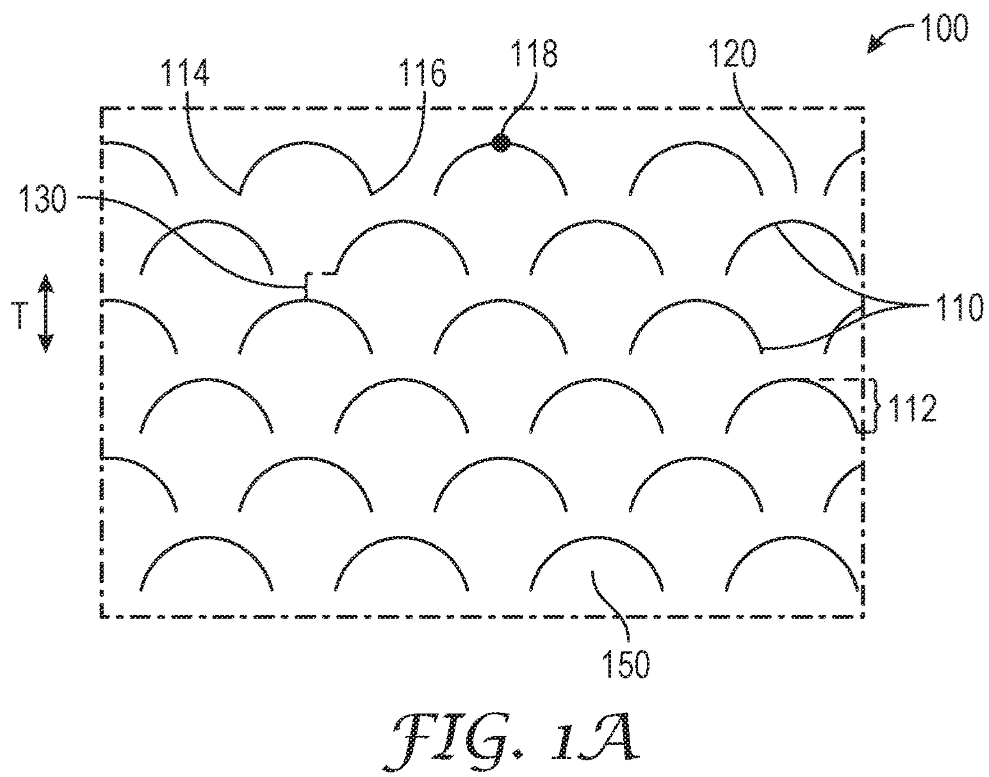
FIG. 1A is a top view of an article of this disclosure, where the article is in an unstretched state.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

A wide range of uses have been developed for non-adhesive elastomeric articles. Many of these articles are designed to self-adhere, that is to say they adhere to themselves without containing a layer of adhesive. One area of particular interest for non-adhesive elastomeric articles is the medical field. Examples of non-adhesive elastomeric articles include compression articles. Examples of compression articles compression stockings, compression sleeves, compression wraps, compression garments, compression tapes, compression bandages, compression dressings, and the like.

Medical articles that provide compression are used in a wide variety of applications. Compression articles are used to apply pressure to a specific area or injury. They help minimize swelling by keeping fluids from gathering at the injury site. Compression can also be applied through the use of compression stockings or compression sleeves, typically used for long term pain or blood circulation management. Among the common conditions where compression wrapping is used include: wrist or ankle sprains; muscle strains; swollen limbs; varicose veins; and contusions or bruises Compression stockings are a specialized hosiery designed to help prevent the occurrence of, and guard against further progression of, venous disorders such as edema, phlebitis and thrombosis. Compression stockings are elastic compression garments worn around the leg, compressing the limb. This reduces the diameter of distended veins and increases venous blood flow velocity and valve effectiveness. Compression therapy helps decrease venous pressure, prevents venous stasis and impairments of venous walls, and relieves heavy and aching legs. A compression sleeve is an elasticized garment that is worn to reduce, for example, the symptoms of lymphedema, such as pain and swelling.

Compression bandages are medical articles that have a wide range of uses. A compression bandage is a long strip of stretchable cloth that can be wrapped around a sprain or strain. Other names for such articles include an "elastic bandage" or a "Tensor bandage". The gentle pressure of the bandage helps reduce swelling, so it may help the injured area feel better. An elastic bandage is a "stretchable bandage used to create localized pressure". Elastic bandages are commonly used to treat muscle sprains and strains by reducing the flow of blood to a particular area by the application of even stable pressure which can restrict swelling at the place of injury. Elastic bandages are also used to treat bone fractures. Padding is applied to the fractured limb, then a splint (usually plaster) is applied. The elastic bandage is then applied to hold the splint in place and to protect it. This is a common technique for fractures which may swell, which would cause a cast to function improperly. These types of splints are usually removed after swelling has decreased and then a fiberglass or plaster cast can be applied.

Due to the risk of latex allergies among users, the original composition of elastic bandages has changed. While some bandages are still manufactured with latex, many woven and knitted elastic bandages provide adequate compression without the use of natural rubber or latex. The modern elastic bandage is typically constructed from cotton, polyester and latex-free elastic yarns. By varying the ratio of cotton, polyester, and the elastic yarns within a bandage, manufacturers are able to offer various grades of compression and durability in their wraps. Often aluminum or stretchable clips are used to fasten the bandage in place once it has been wrapped around the injury. Some elastic bandages even use VELCRO-type closures to secure and stabilize the wrap in place.

Despite the widespread use of these articles, these articles still have a wide range of unmet deficiencies. This disclosure addresses some of the features desired for these types of articles through the formation of mechanically cut patterns in the articles, without changing the composition of the article. Among the features that the cut patterns impart to the elastomeric articles include: providing a method for monitoring the level of tension applied to the article; providing openings for increased breathability such as air flow and moisture transfer; decreasing the effective modulus of elasticity of the article permitting the use of more rigid materials to form the elastomeric articles; and increased surface interactions between layers as the layers are wound upon each other since the application of tension to the article causes the cuts to form shapes that can flex out of the x-y plane of the article. Additionally, the presence of openings in the wrapped articles can in some instances permit viewing through the article to monitor the condition of the layer beneath-either the skin of the user or a lower layer of the wrapped article. The mechanical slit patterns are formed without the removal of material.

The articles described herein define an x-y plane where the x direction is the width of the article and the y direction is the length of the article. The articles also have a thickness (z direction), where the thickness is small relative to the length and width. Out of plane movement is movement in the z direction.

The term "cut" as used herein refers to a narrow opening made in a substrate by the penetration of a cutting tool such that no material is removed from the substrate by the process of cutting. The terms "cuts" and "slits" are used interchangeably.

The term "non-adhesive" as used herein refers to surfaces or layers that do not contain a tacky adhesive layer or a tacky adhesive material and are not tacky but are self-adhesive. By self-adhesive it is meant that when two non-adhesive layers are contacted, they adhere. The non-adhesive layers adhere by affinity. The affinity mechanism of adhesion is often referred to herein as interlocking. The term "interlocking" as used herein refers to the mechanical connection between adjacent layers of material. In this disclosure, this connection is strengthened by the interaction of flaps of material protruding from the adjacent layers, as well as open areas that form in the adjacent layers.

The term "elastomeric" is used consistent with its materials science definition, and refers to any material, such as natural or synthetic rubber, that is able to resume its original shape when a deforming force is removed. An elastomeric layer, in the context of the present disclosure, refers to a layer which can be elastically deformed in at least one direction parallel to its major surfaces. When elongated, expanded or stretched, an elastomeric layer strives to return to its unexpanded shape. When stretching an elongate bandage longitudinally, it strives to return to its unstretched length. Elastic deformation is understood herein to be fully reversible after releasing, while plastic deformation is understood to be not reversible or not fully reversible. Plastic deformation occurs, for example, when a bandage is elongated far enough for elements of it to rupture.

The term "pattern" as used herein refers to a plurality of cuts, where the plurality of cuts forms an array, and the array is in a pattern, where the pattern may be a "random pattern", meaning that there is no readily discernible repeating unit in the array, or the array may be aligned along at least one axis. In some embodiments, the array is aligned along one axis, in other embodiments, the array is aligned along more than one axis. The pattern of slits may be single slits, multi-slits, compound slits, orthogonal slits, or a combination thereof.

The terms "polymer" and "macromolecule" are used herein consistent with their common usage in chemistry. Polymers and macromolecules are composed of many repeated subunits. As used herein, the term "macromolecule" is used to describe a group attached to a monomer that has multiple repeating units. The term "polymer" is used to describe the resultant material formed from a polymerization reaction.

The term "adjacent" as used herein when referring to two layers means that the two layers are in proximity with one another with no intervening open space between them. They may be in direct contact with one another (e.g. laminated together) or there may be intervening layers.

The term "gap" as used herein refers to a void space in a substrate that passes through the entire thickness of the substrate. Gaps can be prepared by cutting, slitting, boring, etc. In the current disclosure, gaps are described as not visible to the naked eye when the substrate is in an unstressed state, and the gaps are described as being visible to the naked eye and as forming "apertures" when in a stressed state. The term "aperture" as used herein is used according to the typical definition and is a space through which light passes. The term "hole" as used herein refers to a void space in the surface of a substrate that is visible to the naked eye in an unstressed state and a stressed state, being an aperture under both an unstressed state and a stressed state.

The term "flap" as used herein refers to a segment of a substrate that upon application of stress is able to move out the x-y plane of the article.

Disclosed herein are non-adhesive articles that comprise an elastomeric layer. The elastomeric layer comprises a plurality of cuts arrayed in a pattern. The cuts are gaps, but the gaps are not visible to the naked eye when the article is in an unstressed state, and in a stressed state, at least some of the cuts become gaps that are that are visible to the naked eye and are perforations in the elastomeric layer. In the stressed state the perforations are apertures through which one can view through the elastomeric layer. The perforations indicate the presence of stress in the article. The elastomeric layer has a lower effective modulus of elasticity in at least one axis than an identical elastomeric layer without the plurality of cuts. Additionally, the elastomeric layer has increased breathability than an identical elastomeric layer without the plurality of cuts, wherein the increased breathability is evidenced by an increased MVTR (Moisture Vapor Transmission Rate). MVTR is a measure of the passage of water vapor through a substance or barrier. MVTR can be measured by a range of different testing methods. In this instance, as the articles are going from a solid layer (the instance where the article does not contain a plurality of cuts) to one in which a plurality of cuts penetrate through the layer, meaning that an increase of MVTR is naturally going to increase.

The articles comprise an elastomeric layer. Elastomeric layers comprise at least one elastomeric material. Elastomeric materials are polymeric materials that are able to resume their original shape when a deforming force is removed. The elastomeric layer has two opposed major surfaces. The elastomeric layer may be an elastic web or an elastic fabric, the web or the fabric having a thickness of, for example, between about 0.1 mm and 5.0 mm.

A wide range of elastomeric materials are suitable for use as the elastomeric layer of the articles. The elastomeric layer may comprise a woven, knitted or a nonwoven web. The web may be a nonwoven fiber web. The woven, knitted or a nonwoven web may comprise a plurality of longitudinally extending elastic yarns, and may also have horizontal elastic yarns.

The elastomeric layer may be a single elastomeric layer or it may comprise one or more additional layers that may or may not be elastomeric layers. In some embodiments, the elastomeric layer is a woven, knitted or a nonwoven web. The woven, knitted or a nonwoven web may be coated or impregnated with a binder or otherwise comprise a binder. The binder may be a polymeric binder. The binder may be adapted such that a portion of its surface adheres to another portion of its surface when the portions are brought into contact. This property of being "capable of adhering to itself" is referred to herein as the binder—or a surface coated with it—being "non-adhesive". The polymeric binder may be an elastomeric polymeric binder or a non-elastomeric polymeric binder. Suitable elastomeric polymeric binders may comprise natural rubber latex, a synthetic latex, such as homopolymer and copolymer latexes of acrylics, butadienes, styrene/butadiene rubbers, chloroprenes, ethylenes (e.g., vinyl acetate/ethylene), isoprenes, nitriles and urethanes, or mixtures thereof. Examples of suitable polymeric elastomeric binders are disclosed for example in U.S. Pat. Nos. 3,575,782; 4,984,585; and 6,155,424.

The elastomeric layer comprises a plurality of cuts, where the plurality of cuts is arrayed in a pattern. In some embodiments, the pattern may be random, in other embodiments the pattern may be arrayed along at least one axis. The cuts are not perforations because they are not formed by removing material from the substrate layer, but rather are cuts that are gaps, but the gaps are not visible to the naked eye when the adhesive article is in an unstressed state, but when the adhesive article is in a stressed state at least some of the gaps are visible to the naked eye.

The use of cuts rather than perforations has a variety of advantages. Among the advantages is that the cuts are able to reduce the effective modulus without removing material from the elastomeric layer. The array of cuts also provides improved MVTR. An advantage of the use of cuts instead of perforations is that the array of cuts form gaps that provide a visual indicator of the application of stress to the elastomeric article. As mentioned above, the cuts are gaps that are not visible to the naked eye when the elastomeric article is in an unstressed state, but upon the application of stress at least some of the gaps become visible to the naked eye. In this way, the elastomeric layer itself is able to indicate when stress is applied to the elastomeric article. Thus, the cuts not only provide a method for mitigating the effects of stress on the elastomeric article but also provide a method for visibly detecting when stress is applied to the elastomeric article.

The plurality of cuts can be made in a number of different ways as long as the method does not involve removing material from the elastomeric layer and the cuts form gaps that are essentially not visible to the naked eye in the unstressed state and at least some of gaps become visible to the naked eye when the adhesive article is in a stressed state. Among the methods are those in which the cuts are introduced into the elastomeric layer when the layer is formed for example by extrusion, molding, machining and the like. Other methods are those in which the cuts are introduced into the substrate layer after the substrate layer is formed such as by cutting using a cutting tool such as a knife, a linear blade, a rotary die blade, a water jet, or a laser beam, or by stamping using a stamping tool. In some embodiments, the cuts are made by feeding the elastomeric layer into a nip containing a rotary die blade and an anvil such that the die cuts through the elastomeric layer to form the cut pattern.

The elastomeric layer of the present articles has a lower effective modulus of elasticity in at least one axis than an identical elastomeric layer without the plurality of cuts. In other words, modifying the elastomeric layer with a plurality of cuts reduces the effective modulus of elasticity. The elastic modulus (also known as the modulus of elasticity) is a quantity that measures an object or substance's resistance to being deformed elastically (i.e., non-permanently) when a stress is applied to it. The elastic modulus of an object is defined as the slope of its stress-strain curve in the elastic deformation region. Effective modulus of elasticity is defined in the art as the ratios of the average stresses to the average strains that result in the body when it is subject to pure shear or pure compression on its outer boundary. In the current disclosure, the effective elastic modulus is the elastic modulus of the elastomeric layer or article that has been modified by cutting.

In some embodiments, the plurality of cuts is arrayed in a pattern along one axis or more than one axis. The plurality of cuts comprises patterns of single slits, multi-slits, compound slits, orthogonal slits, and combinations thereof. The plurality of cuts, upon the application of stress form shaped gaps that indicate the magnitude of the stress applied to the article.

A wide variety of methods can be used to form the plurality of cuts. Among the suitable methods are extrusion, molding, laser cutting, water jetting, machining, stereolithography or other 3D printing techniques, laser ablation, photolithography, chemical etching, rotary die cutting, stamping, other suitable negative or positive processing techniques, or combinations thereof.

Upon application of stress to the elastomeric layer, the material expands. The application of stress comprises wrapping, bending, stretching, swelling or a combination thereof. The application of stress causes one or more of (1) the cuts to form openings and/or (2) the material adjacent to the cuts to form flaps. In some embodiments, applying stress to the article causes the material to change from a two-dimensional structure to a three-dimensional structure. In some embodiments, when exposed to stress, at least one of (1) the terminal ends of the slits in the elastomeric layer are drawn toward one another, causing a flap of the elastomeric layer to move or buckle upward relative to the plane of the material in its unstressed state and/or (2) portions of the elastomeric layer to move or buckle downward relative to the plane of the elastomeric layer in its unstressed state forming an opening portion. In some embodiments, the flaps have a flap shape that is at least one of scale-shaped, curved, rectangular, pointed, cusp-shaped, or combinations thereof. In some embodiments, stretching of the non-adhesive article in a lengthwise direction (y axis) causes gaps and flaps to form, wherein the gaps and flaps interact with each other to form increased interfacial adhesion between overlapped layers of the non-adhesive article upon wrapping, typically wrapping the article around an item. In some embodiments, the elastomeric layer is wrapped around the item at least two fully wraps such that at least one of the flaps, openings, and/or interlocking features on the first layer or wrap interlock with at least one of the flaps, openings, and/or interlocking features on the second layer or wrap. Additionally, if the wound to which the article is wrapped swells, the swelling tension can be detectable by an increase in the size and/or shape of the slits. While the size and/or shape of the slits increase, it should be understood that the actual relationship between the size and shape of the opening formed by the slit and the amount of extension applied is a complicated relationship and may not be mathematically proportional. The size and shape of the openings formed by placing the slit article under stress may vary depending upon the viewing angle for example. However, the general concept is that the open area increases with the level of stretching or extension of the article, and is repeatable enough to provide a consistent reference for application of compression.

Various embodiments of the present disclosure relate to multi-slit patterns and to articles including these multi-slit patterns.

As used herein, the term "double slit pattern" refers to a pattern of a plurality of individual slits. Each slit in the plurality can be formed by a single continuous cut that does not crossover or intersect itself. The pattern includes a plurality of rows of slits and the individual slits in a first row are substantially aligned with the individual slits in a directly adjacent, second row. A double slit is comprised of a slit in a first row that is substantially aligned with a slit in a second row. Together, these two substantially aligned slits form a double slit.

As used herein, the term "triple slit pattern" refers to refers to a pattern of a plurality of individual slits. Each slit in the plurality can be formed by a single continuous cut that does not crossover or intersect itself. The pattern includes a plurality of rows of slits and the individual slits in a first row are substantially aligned with the individual slits in a directly adjacent, second row. The slits in the second row are substantially aligned with the individual slits in a directly adjacent, third row. A triple slit is comprised of a slit in a first row that is substantially aligned with a slit in a second row, both of which are substantially aligned with a slit in a third row. Together, these three substantially aligned slits form a triple slit.

As used herein, the term "quadruple slit pattern" refers to refers to a pattern of a plurality of individual slits. Each slit in the plurality can be formed by a single continuous cut that does not crossover or intersect itself. The pattern includes a plurality of rows of slits and the individual slits in a first row are substantially aligned with the individual slits in a directly adjacent, second row. The slits in the second row are substantially aligned with the individual slits in a directly adjacent, third row. The slits in the third row are substantially aligned with the individual slits in a directly adjacent, fourth row. A quadruple slit is comprised of a slit in a first row that is substantially aligned with a slit in a second row, both of which are substantially aligned with a slit in a third row, all three of which are substantially aligned with a slit in a fourth row. Together, these four substantially aligned slits form a quadruple slit.

The term "multi-slit pattern" includes double slit patterns, triple slit patterns, quadruple slit patterns, etc. Further, the term "multi-slit pattern" is meant to include any slit pattern wherein two or more slits that are each in different, directly adjacent rows substantially align with one another such that their terminal ends substantially align. Substantial alignment of the terminal ends of aligned multi-slits means that if you draw an imaginary line between two aligned terminal ends in two adjacent slits of the multi-slit, the angle of that imaginary line relative to the alignment axis (the axis that is perpendicular to the row(s)) is no greater than +/−20 degrees. In some embodiments, the length of each slit that forms a multi-slit differs by no more than +/−20% of the total length of the longest or shortest slit. In some embodiments, where the slits are linear, they are substantially parallel to one another. In some embodiments where the slits are not linear, the aligned multi-slits are all substantially aligned parallel to the tension axis within +/−20 degrees.

Double, triple, quadruple, or multi-slit patterns create significantly more out of plane undulation than single slit patterns when exposed to tension along a tension axis. This out of plane undulation of the material has great value for many applications. For example, these out of plane undulation areas create out of plane material or loops that can interlock with other areas of out of plane material or loops when portions of the material are placed adjacent to one another or wrapped together. As such, multi-slit patterns inherently interlock and/or include interlocking features. Once tension-activated, these features and patterns interlock and hold the material substantially in place. Examples of the wide range of suitable patterns are demonstrated in a series of patterns filed on the same day (Dec. 23, 2019) in U.S. Patent Application Nos. 62/952,778, 62/952,789, 62/952,806, 62/952,815, 62/952,840, and 62/953,042.

Interlocking can be measured by the following test method. A sample measuring 736-inches (0.91 m) long and 7.5-inches (19 cm) wide was obtained. The sample was fully deployed without tearing, and was then placed directly adjacent to a smooth PVC pipe (for example, a one having an outer diameter (OD) of 3.15 inches (8 cm) and a length of 23 inches (58.4 cm)), ensuring that the sample remained fully deployed during rolling. The sample was wrapped over the pipe ensuring that each successive layer was placed directly over the previous layer and that the sample was placed at the center (along the length) of the pipe. The same will provide a minimum of two complete wraps around the pipe. When all the sample was wrapped around the pipe, the sample was released and whether the sample unfolded/unwrapped was observed. If the sample did not unfold/unwrap after a 1-minute wait, the sample was slid off the pipe onto a smooth surface such as a table top. The sample was then lifted by the trailing edge to see if it unrolled/unwrapped or held its shape.

In some embodiments, the non-adhesive article comprises a compression article. Examples of suitable compression articles are compression stockings, compression sleeves, compression wraps, compression garments, compression tapes, compression bandages, and compression dressings.

Compression bandages are particularly suitable non-adhesive articles of this disclosure. In many embodiments, the compression bandages comprise at least one additional layer adjacent to the elastomeric layer. The additional layer or layers may be elastomeric layers or they may be non-elastomeric layers. In some embodiments, the compression bandage further comprises at least one non-elastomeric layer, wherein the at least one non-elastomeric layer comprises cuts that are aligned with cuts in the elastomeric layer, and wherein the compression bandage is capable of wrapping upon itself such that the overlapping portions of the article self-adhere. Suitable elastomeric and non-elastomeric layers are described above.

The desirable features described above are particularly desirable for compression bandages. The presence of the cuts permits the level of stress to which the bandage is applied to be gauged by the user. Additionally, the presence of the cuts aids in increasing the breathability of the bandage as evidenced by increased MVTR. Additionally, as described above, stretching of the compression bandage in a lengthwise direction (y axis) causes gaps and flaps to form, where the gaps and flaps interact with each other to form increased interfacial adhesion between overlapped layers of the compression bandage upon wrapping.

Also disclosed herein are methods of using non-adhesive articles. These methods comprise preparing a non-adhesive article and wrapping the non-adhesive article upon itself such that the overlapping portions of the article self-adhere. The non-adhesive articles are described in detail above and comprise an elastomeric layer, where the elastomeric layer comprises a plurality of cuts, where the plurality of cuts is arrayed in a pattern. The cuts are gaps, but the gaps are not visible to the naked eye when the non-adhesive article is in an unstressed state, and in a stressed state, at least some of the cuts become gaps that are that are visible to the naked eye and are perforations in the elastomeric layer such that in a stressed state the perforations are apertures through which one can view through the non-adhesive article. The perforations indicate the presence of stress in the non-adhesive article. The elastomeric layer has a lower effective modulus of elasticity in at least one axis than an identical elastomeric layer without the plurality of cuts, and the non-adhesive article has increased breathability than an identical non-adhesive article without the plurality of cuts. Increased breathability is evidenced by an increased MVTR (Moisture Vapor Transmission Rate).

The articles comprise an elastomeric layer. Elastomeric layers comprise at least one elastomeric material. Elastomeric materials are polymeric materials that are able to resume their original shape when a deforming force is removed. The elastomeric layer has two opposed major surfaces. The elastomeric layer may be an elastic web or an elastic fabric, the web or the fabric having a thickness of, for example, between about 0.1 mm and 5.0 mm.

A wide range of elastomeric materials are suitable for use as the elastomeric layer of the articles. The elastomeric layer may comprise a woven, knitted or a nonwoven web. The web may be a nonwoven fiber web. The woven, knitted or a nonwoven web may comprise a plurality of longitudinally extending elastic yarns.

The elastomeric layer may be a single elastomeric layer or it may comprise one or more additional layers that may or may not be elastomeric layers. In some embodiments, the elastomeric layer is a woven, knitted or a nonwoven web. The woven, knitted or a nonwoven web may be coated or impregnated with a binder or otherwise comprise a binder. The binder may be a polymeric binder. The binder may be adapted such that a portion of its surface adheres to another portion of its surface when the portions are brought into contact. This property of being "capable of adhering to itself" is referred to herein as the binder—or a surface coated with it—being "non-adhesive". The polymeric binder may be an elastomeric polymeric binder or a non-elastomeric polymeric binder. Suitable elastomeric polymeric binders may comprise natural rubber latex, a synthetic latex, such as homopolymer and copolymer latexes of acrylics, butadienes, styrene/butadiene rubbers, chloroprenes, ethylenes (e.g., vinyl acetate/ethylene), isoprenes, nitriles and urethanes, or mixtures thereof. Examples of suitable polymeric elastomeric binders are disclosed for example in U.S. Pat. Nos. 3,575,782; 4,984,585; and 6,155,424.

As mentioned above, a wide variety of techniques can be used to form the plurality of cuts in the non-adhesive articles. The plurality of cuts can be made in a number of different ways as long as the method does not involve removing material from the elastomeric layer and the cuts form gaps that are essentially not visible to the naked eye in the unstressed state and at least some of gaps become visible to the naked eye when the adhesive article is in a stressed state. Among the methods are those in which the cuts are introduced into the elastomeric layer when the layer is formed for example by extrusion, molding, machining and the like. Other methods are those in which the cuts are introduced into the substrate layer after the substrate layer is formed such as by cutting using a cutting tool such as a knife, a linear blade, a rotary die blade, a water jet, or a laser beam, or by stamping using a stamping tool. In some embodiments, the cuts are made by feeding the elastomeric layer into a nip containing a rotary die blade and an anvil such that the die cuts through the elastomeric layer to form the cut pattern.

The plurality of cuts is arrayed in a pattern along one axis or more than one axis. The plurality of cuts comprises patterns of single slits, multi-slits, compound slits, orthogonal slits, and combinations thereof. The plurality of cuts, upon the application of stress form shaped gaps that indicate the magnitude of the stress applied to the article. The arrays of cuts are described in detail above.

The plurality of cuts forms shaped gaps that indicate the magnitude of the stress applied to the article. The stress comprises wrapping, bending, stretching or a combination thereof.

In some embodiments, the non-adhesive article comprises a compression article. Examples of suitable compression articles are compression stockings, compression sleeves, compression wraps, compression garments, compression tapes, compression bandages, and compression dressings as described above.

In some embodiments, the article comprises a compression bandage, where the compression bandage further comprises at least one non-elastomeric layer, wherein the at least one non-elastomeric layer comprises cuts that are aligned with cuts in the elastomeric layer. Upon application of stress to the compression bandage, the material expands. The application of stress comprises wrapping, bending, stretching or a combination thereof. The application of stress causes one or more of (1) the slits to form openings and/or (2) the material adjacent to the slits to form flaps. In some embodiments, applying stress to the article causes the material to change from a two-dimensional structure to a three-dimensional structure. In some embodiments, when exposed to stress, at least one of (1) the terminal ends of the slits in the elastomeric layer are drawn toward one another, causing a flap of the elastomeric layer to move or buckle upward relative to the plane of the material in its unstressed state and/or (2) portions of the elastomeric layer to move or buckle downward relative to the plane of the elastomeric layer in its unstressed state forming an opening portion. In some embodiments, the flaps have a flap shape that is at least one of scale-shaped, curved, rectangular, pointed, cusp-shaped, or combinations thereof. In some embodiments, stretching of the non-adhesive article in a lengthwise direction (y axis) causes gaps and flaps to form, wherein the gaps and flaps interact with each other to form increased interfacial adhesion between overlapped layers of the non-adhesive article upon wrapping, typically wrapping the article around an item. In some embodiments, the elastomeric layer is wrapped around the item at least two fully wraps such that at least one of the flaps, openings, and/or interlocking features on the first layer or wrap interlock with at least one of the flaps, openings, and/or interlocking features on the second layer or wrap.

The disclosure may be further understood by referring to the drawings. One exemplary embodiment of a single slit pattern is shown schematically in FIG. 1A. The single-slit pattern is formed in material 100 and includes a plurality of slits 110 that each include a first terminal end 114, a second terminal end 116, and a midpoint 118. A plurality of individual slits 110 are aligned to form rows 112 that are generally perpendicular to tension axis T. Material 120 is present between adjacent slits 110 in a row 112. The material between directly adjacent rows 112 of slits 110 forms beams 130. Beams 130 are regions between adjacent coaxial rows of slits. In the exemplary embodiment of FIG. 1A, slits 110 are not straight lines but are instead curved single slits. In the embodiment of FIG. 1A, the ends of the slits are curved. The degree of curvature shown in FIG. 1A is approximately a semi-circle in shape, but the degree of curvature and slit length can vary. The flap region 150 is generally the area enclosed by the path of slit 110 and the imaginary straight line between terminal ends 114 and 116. Those of skill in the art will appreciate that many changes may be made to the pattern while still falling within the scope of the present disclosure. For example, in some embodiments, the shape will be elliptical. Alternatively, the slit length, row size or shape, and beam size or shape can vary. Further, the degrees of offset or phase offset can vary from what is shown.

Figure 1B:
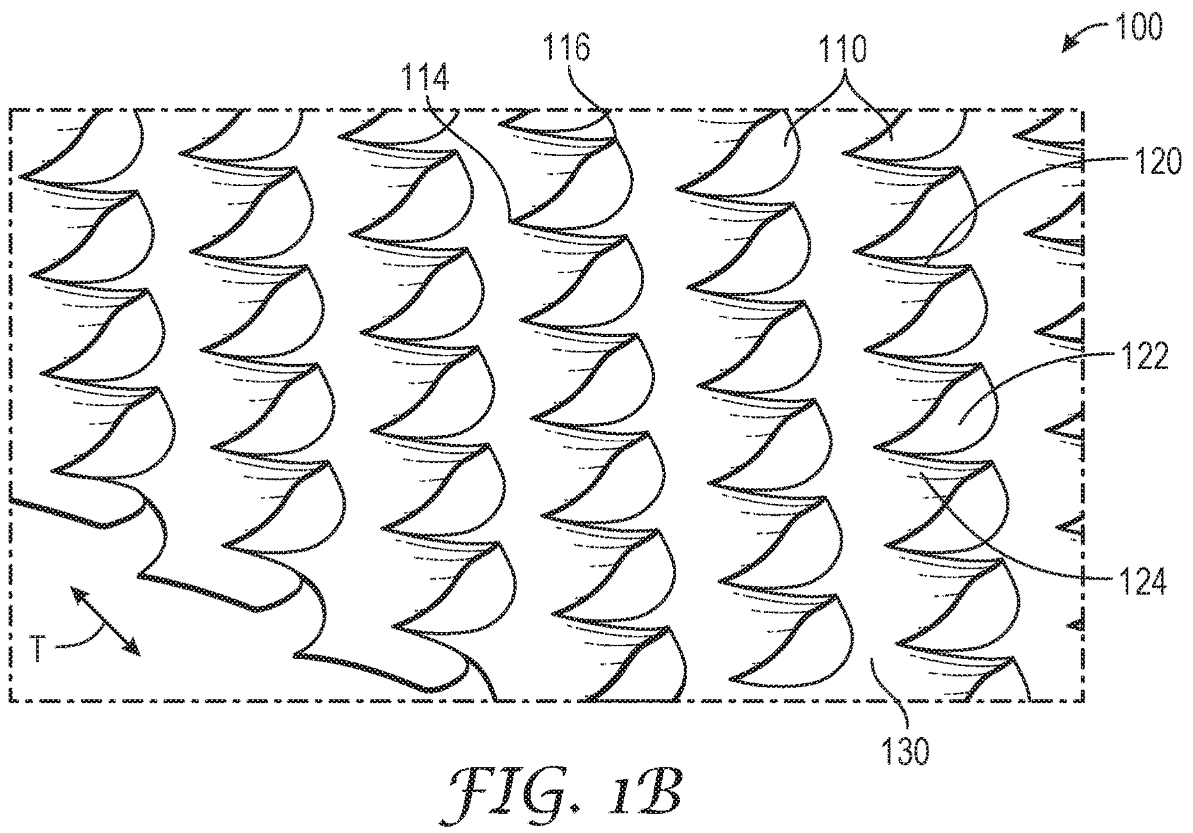
FIG. 1B is a three-quarter view of the article of 1A, where the article is in a stretched state.

FIG. 1B shows a three-quarter view of the article of FIG. 1A where the pattern of FIG. 1A formed in an article has been exposed to tension along the tension axis T. When material 100 is tension activated or deployed along tension axis T, portions of material 100 experiences tension and/or compression that causes material 100 to move out of the original plane of material 100 in its non-tensioned format. When exposed to tension along the tension axis, terminal ends 114, 116 experience compression and are drawn toward one another, causing a flap region to move or buckle upward relative to the horizontal plane of the material 100 in its untensioned state (FIG. 1A), creating a flap 124. Portions of beams 130 move or buckle downward relative to the horizontal plane of the material 100 in its untensioned state (FIG. 1A), forming an opening portion 122. The material 120 between adjacent slits 110 in a row primarily experiences tension perpendicular to the tension axis T. This region or area does not move substantially out of the original plane and instead bends slightly as compared to the untensioned form of FIG. 1A. These movements in material 100 form a series of bent, fish-scale-like protrusions.

Figure 2A:
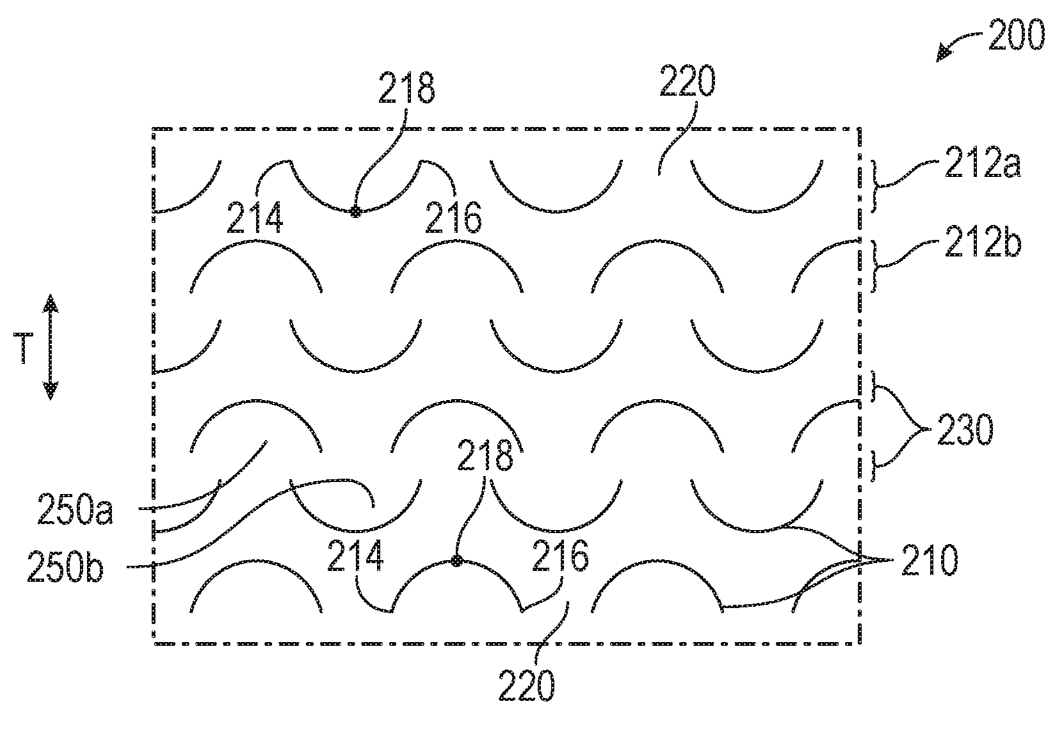
FIG. 2A is a top view of another article of this disclosure, where the article is in an unstretched state.

Another exemplary embodiment of a single slit pattern is shown schematically in FIG. 2A. The pattern of FIG. 2A shows that differing rows can have differently positioned slits. In other words, the slits in a single row all have the same position, but the slit position varies in differing rows (e.g. directly adjacent rows). The single-slit pattern of FIG. 2A includes a first set of rows **212*a* that include slits 210 of a first shape and position and a second set of rows 212*b* that includes the same slit shape but the slits 210 are positioned differently (in this case, inverted). Each slit has terminal ends 214 and 216 and midpoint 218. The slit shape in both the first set of rows 212*a* and the second set of rows 212*b* is substantially similar to that of FIG. 1A, whose description above is repeated herein. Material 220 is present between adjacent slits 210 in a row 212. The material between directly adjacent rows 212 of slits 210 forms beams 230. The flap regions 250*a* and 250*b* are generally the area enclosed by the path of slit 210 and the imaginary straight line between terminal ends 214 and 216**. In this exemplary embodiment, the slits have two terminal ends. A straight, imaginary line extends between and connects these terminal ends. In this embodiment, the straight, imaginary line extending between and connecting the terminal ends of a first slit is substantially colinear with the straight, imaginary line extending between and connecting the terminal ends of a directly adjacent slit. In this exemplary embodiment, all of the straight, imaginary lines extending between and connecting the slit terminal ends in a row are approximately colinear. Those of skill in the art will appreciate that many changes may be made to the pattern while still falling within the scope of the present disclosure. Those of skill in the art will appreciate that the shape and slit length can vary. Further, any slit shapes can be used. Further, the pattern can alternate in 2 rows, 3 rows, 4 rows, etc. Alternatively, the slit length, row size or shape, and beam size or shape can vary. Further, the degrees of offset or phase offset can vary from what is shown.

Figure 2B:
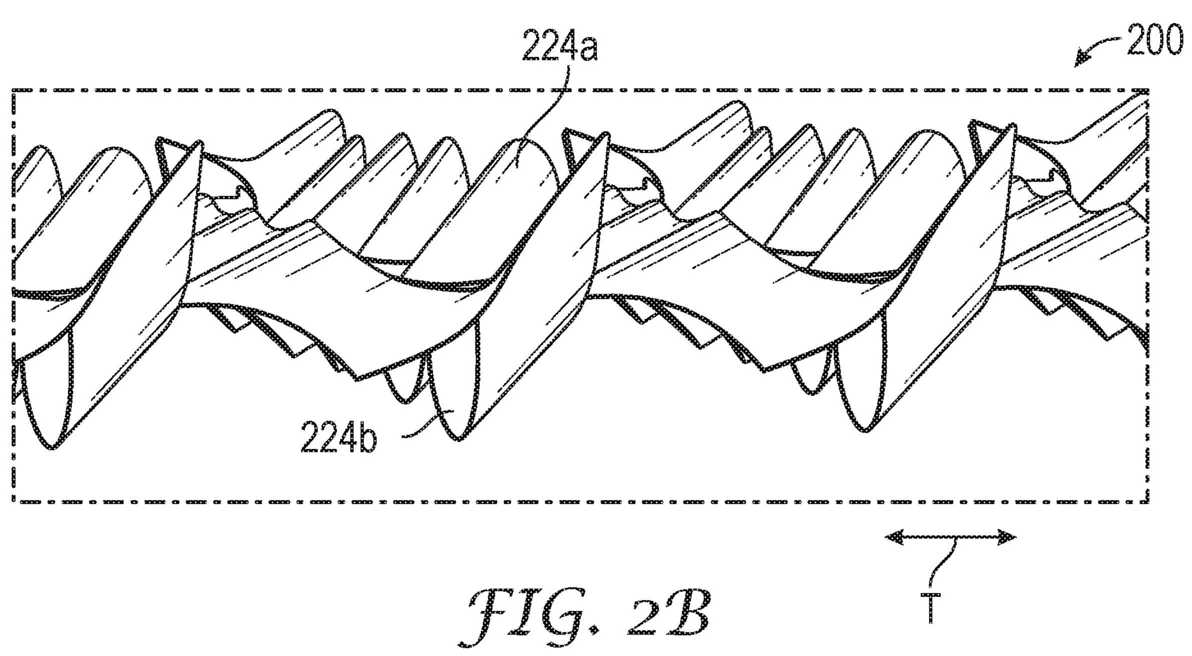
FIG. 2B is a side view of the article of 2A, where the article is in a stretched state.

FIG. 2B shows a side view of the pattern of FIG. 2A formed and exposed to tension along the tension axis T. When material 200 is tension activated or deployed along tension axis T, portions of material 200 experiences tension and/or compression that causes the material to move out of the original plane of material 200 in its non-tensioned format. Exposure to stretching along tension axis T creates flaps **224*a* and 224*b***.

FIGS. 3-8 are photographs of articles of this disclosure and of methods of using these articles. FIG. 3A is a photograph of an article of this disclosure, where the article is in a low stretched state. The low stretched state means that minimal tension is applied to the article. It is understood in the art that elastomeric non-adhesive articles typically require at least minimal stretching to be held in place. The article has a pattern of slits like the pattern shown in the schematic of FIG. 2A. The article has a ruler adjacent next to it and two pieces of tape to mark reference points against the ruler, where the two pieces of tape are approximately 1 inch (2.54 centimeters) apart.

Figure 3A:
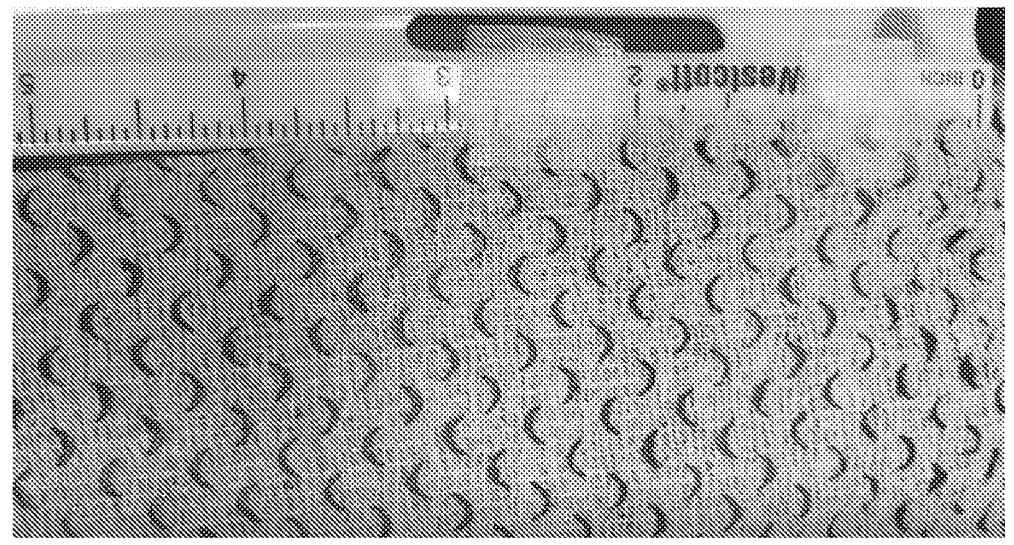
FIG. 3A is a photograph of an article of this disclosure, where the article is in an low stretched state.
Figure 3B:
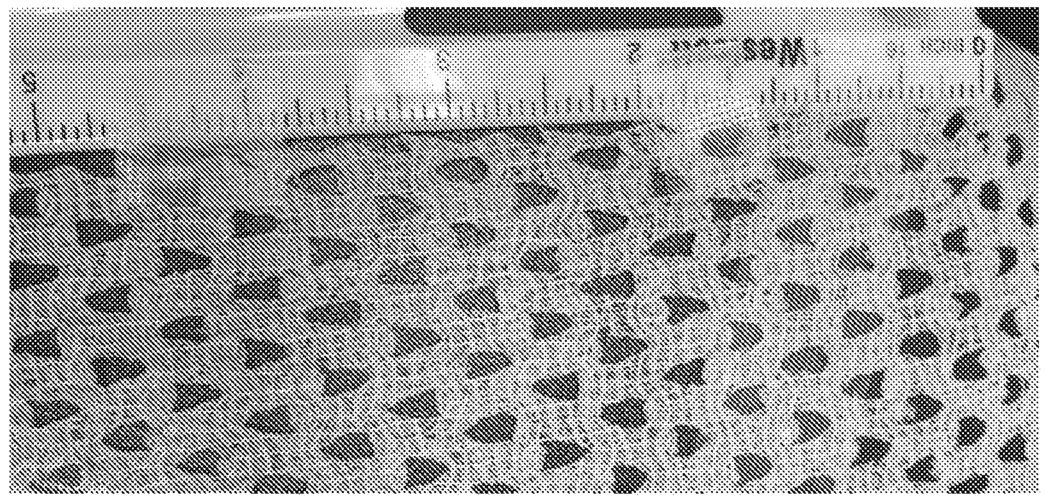
FIG. 3B is a photograph of the article of 3A, where the article is in a higher stretched state.

FIG. 3B is a photograph of the article of FIG. 3A in a higher stretched state. The article is stretched and held such that the tape markers are approximately 2 inches (5.08 centimeters) apart. The semicircular slits have opened to form apertures.

Figure 4A:
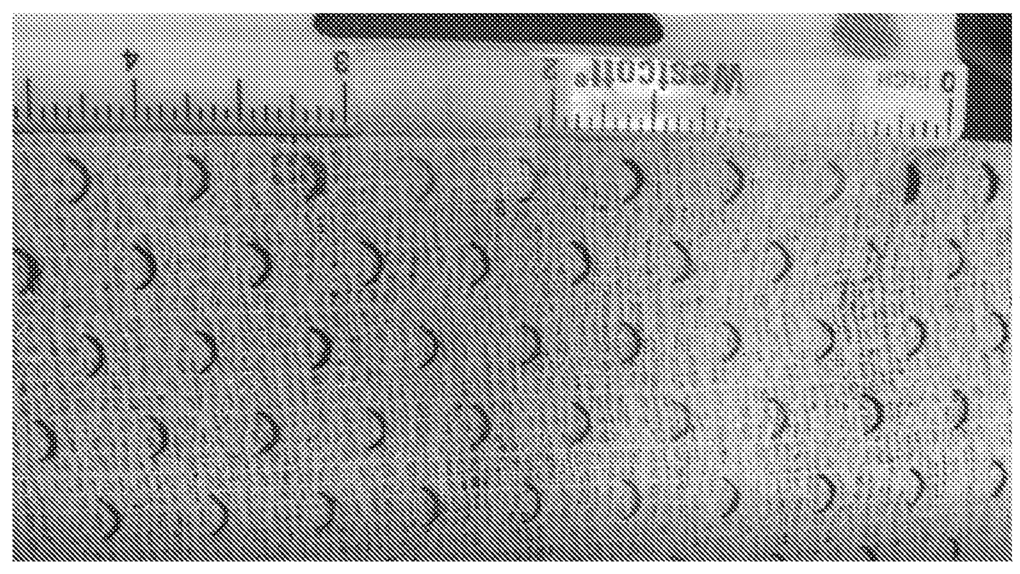
FIG. 4A is a photograph of another article of this disclosure, where the article is in a low stretched state.

FIG. 4A is a photograph of an article of this disclosure, where the article is in a low stretched state. The article has a pattern of slits like the pattern shown in the schematic of FIG. 1A. The article has a ruler adjacent next to it and two pieces of tape to mark reference points against the ruler, where the two pieces of tape are approximately 1 inch (2.54 centimeters) apart.

Figure 4B:
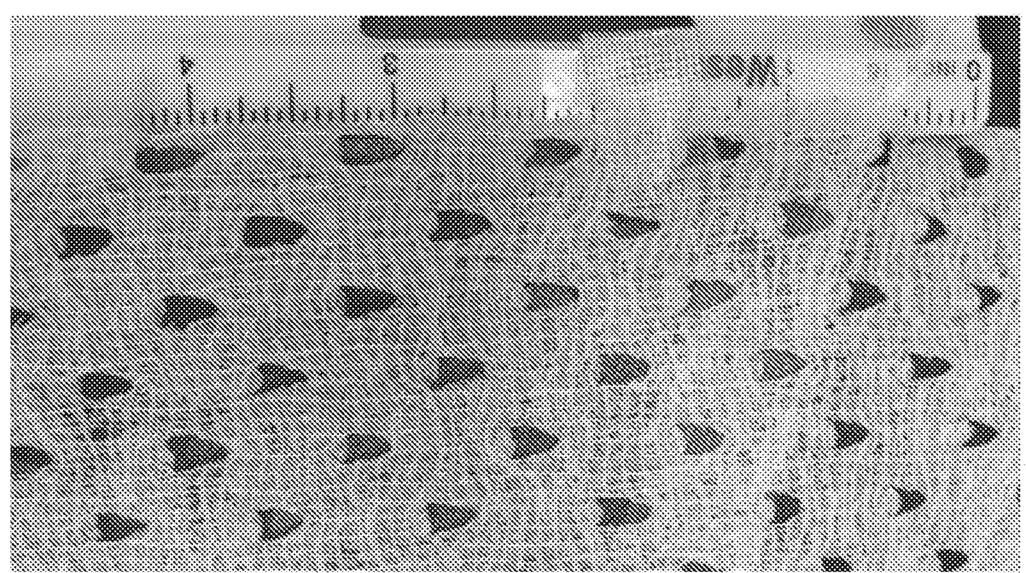
FIG. 4B is a photograph of the article of 4A, where the article is in a higher stretched state.

FIG. 4B is a photograph of the article of FIG. 4A in a higher stretched state. The article is stretched and held such that the tape markers are approximately 2 inches (5.08 centimeters) apart. The semicircular slits have opened to form apertures.

Figure 5A:
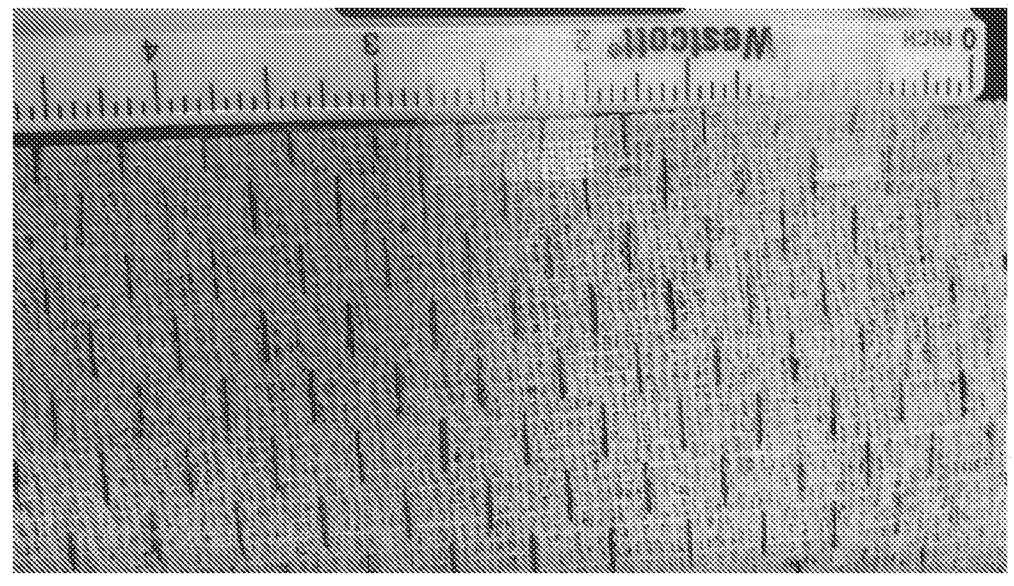
FIG. 5A is a photograph of another article of this disclosure, where the article is in a low stretched state.

FIG. 5A is a photograph of an article of this disclosure, where the article is in a low stretched state. The article has a pattern of linear slits. The article has a ruler adjacent next to it and two pieces of tape to mark reference points against the ruler, where the two pieces of tape are approximately 1 inch (2.54 centimeters) apart.

Figure 5B:
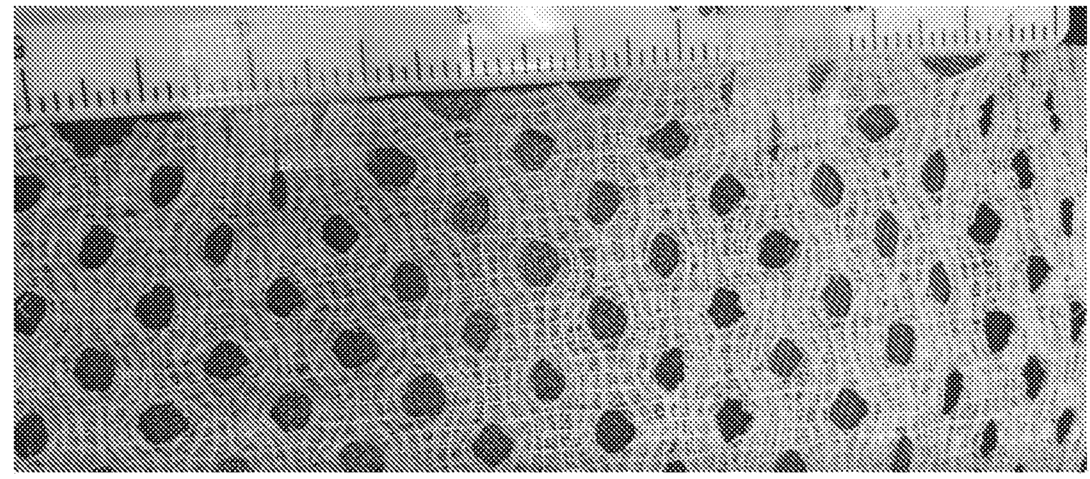
FIG. 5B is a photograph of the article of 5A, where the article is in a higher stretched state.

FIG. 5B is a photograph of the article of FIG. 5A in a higher stretched state. The article is stretched and held such that the tape markers are approximately 2 inches (5.08 centimeters) apart. The linear slits have opened to form apertures.

Figure 6A:
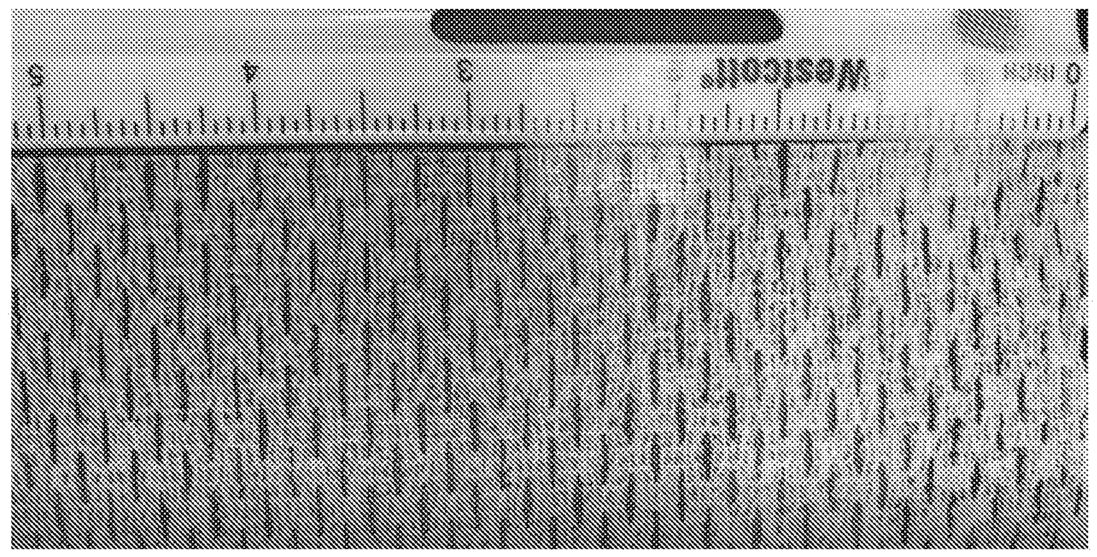
FIG. 6A is a photograph of another article of this disclosure, where the article is in a low stretched state.

FIG. 6A is a photograph of an article of this disclosure, where the article is in a low stretched state. The article has a pattern of linear slits, where the linear slits are closer to each other than in the pattern of FIG. 5A. The article has a ruler adjacent next to it and two pieces of tape to mark reference points against the ruler, where the two pieces of tape are approximately 1 inch (2.54 centimeters) apart.

Figure 6B:
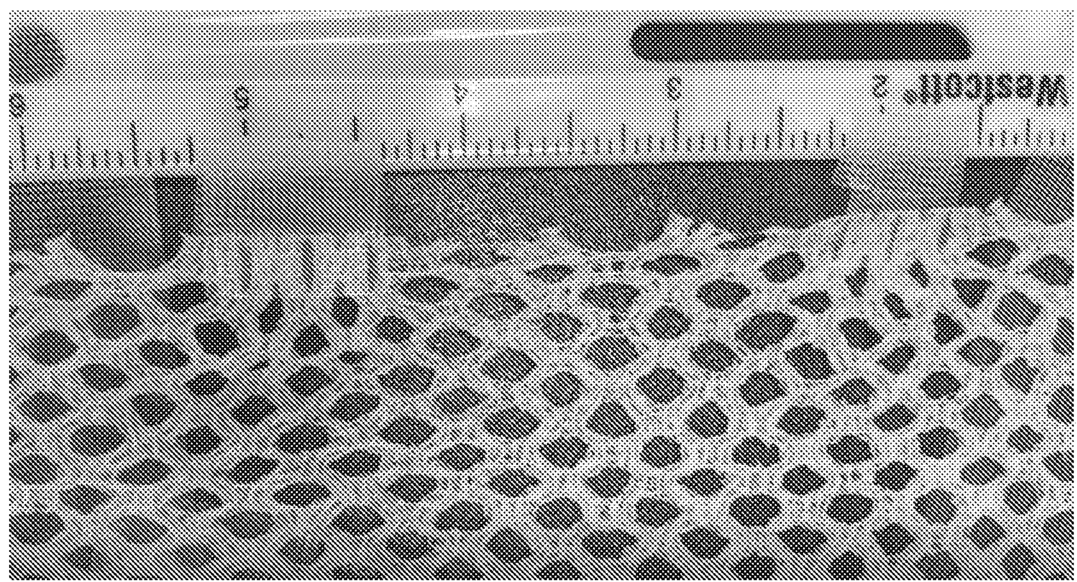
FIG. 6B is a photograph of the article of 6A, where the article is in a higher stretched state.

FIG. 6B is a photograph of the article of FIG. 6A in a higher stretched state. The article is stretched and held such that the tape markers are approximately 2 inches (5.08 centimeters) apart. The linear slits have opened to form apertures.

Figure 7A:
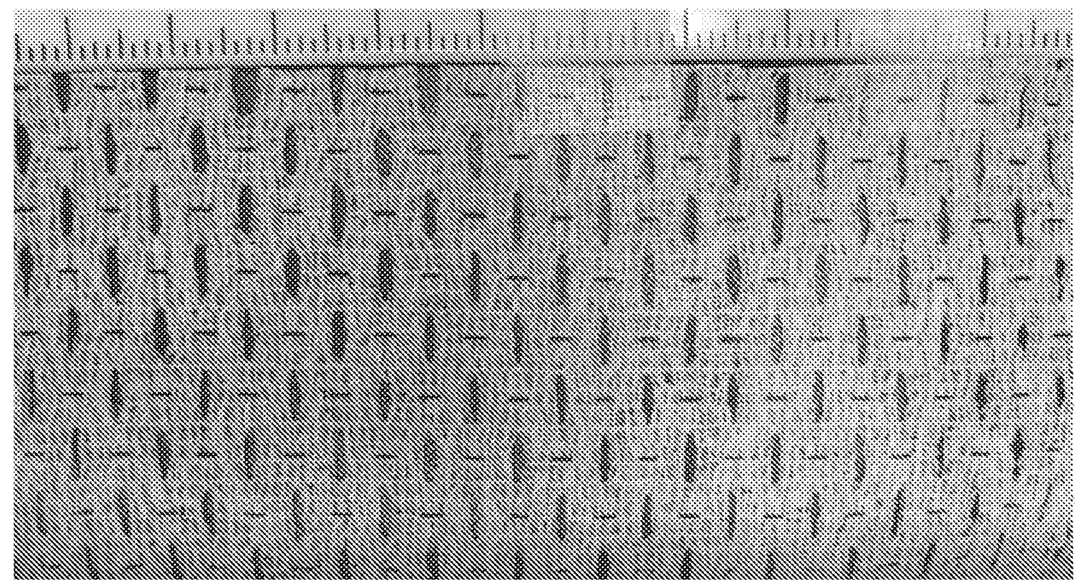
FIG. 7A is a photograph of another article of this disclosure, where the article is in a low stretched state.

FIG. 7A is a photograph of an article of this disclosure, where the article is in a low stretched state. The article has a pattern of two sets of orthogonal linear slits. The article has a ruler adjacent next to it and two pieces of tape to mark reference points against the ruler, where the two pieces of tape are approximately 1 inch (2.54 centimeters) apart.

Figure 7B:
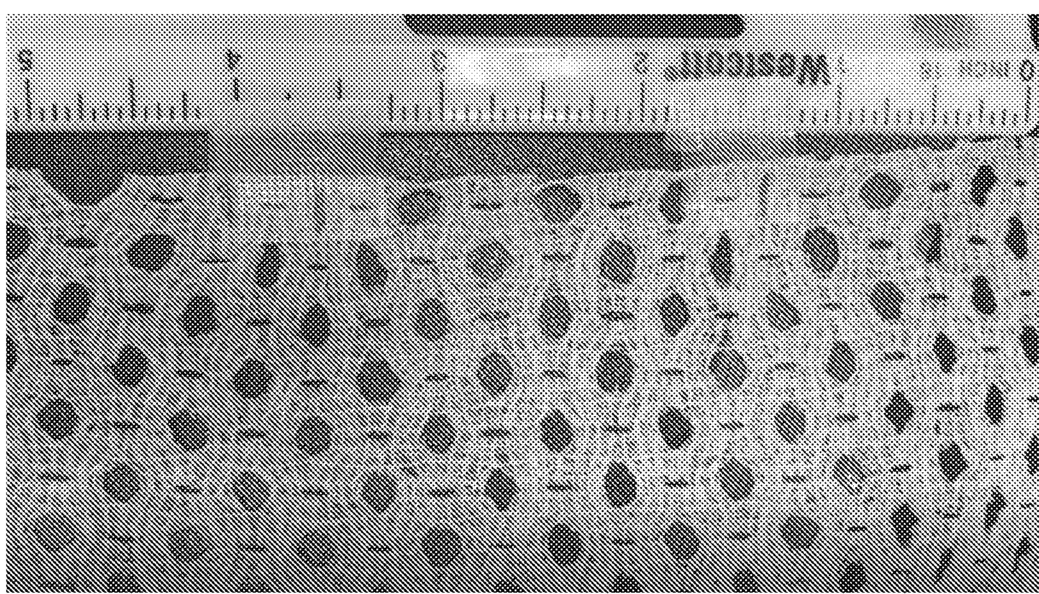
FIG. 7B is a photograph of the article of 7A, where the article is in a higher stretched state.

FIG. 7B is a photograph of the article of FIG. 7A in a higher stretched state. The article is stretched and held such that the tape markers are approximately 2 inches (5.08 centimeters) apart. Both sets of linear slits have opened to form apertures.

Figure 8A:
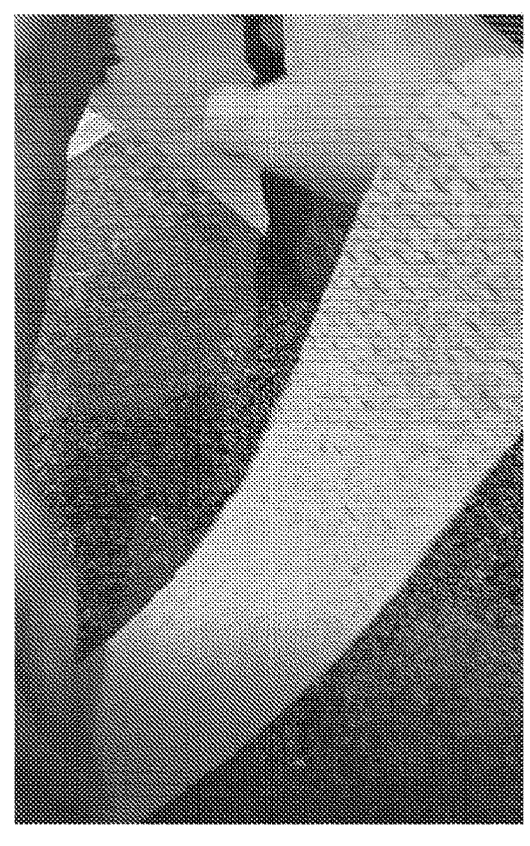
FIGS. 8A-8E are photographs showing an article of this disclosure, in a stretched state, being wrapped around a wrist.
Figure 8B:
Figure 8C:
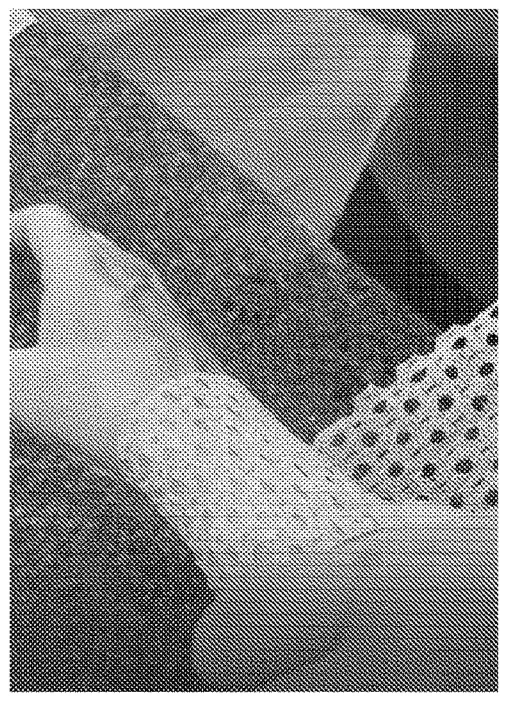
Figure 8D:
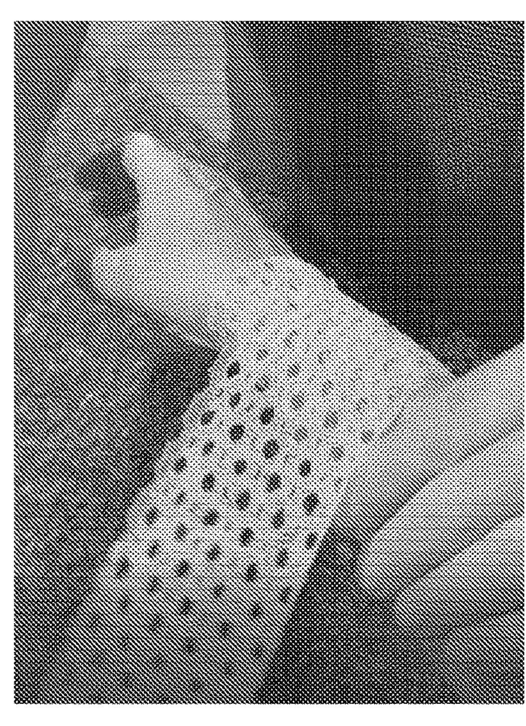
Figure 8E:
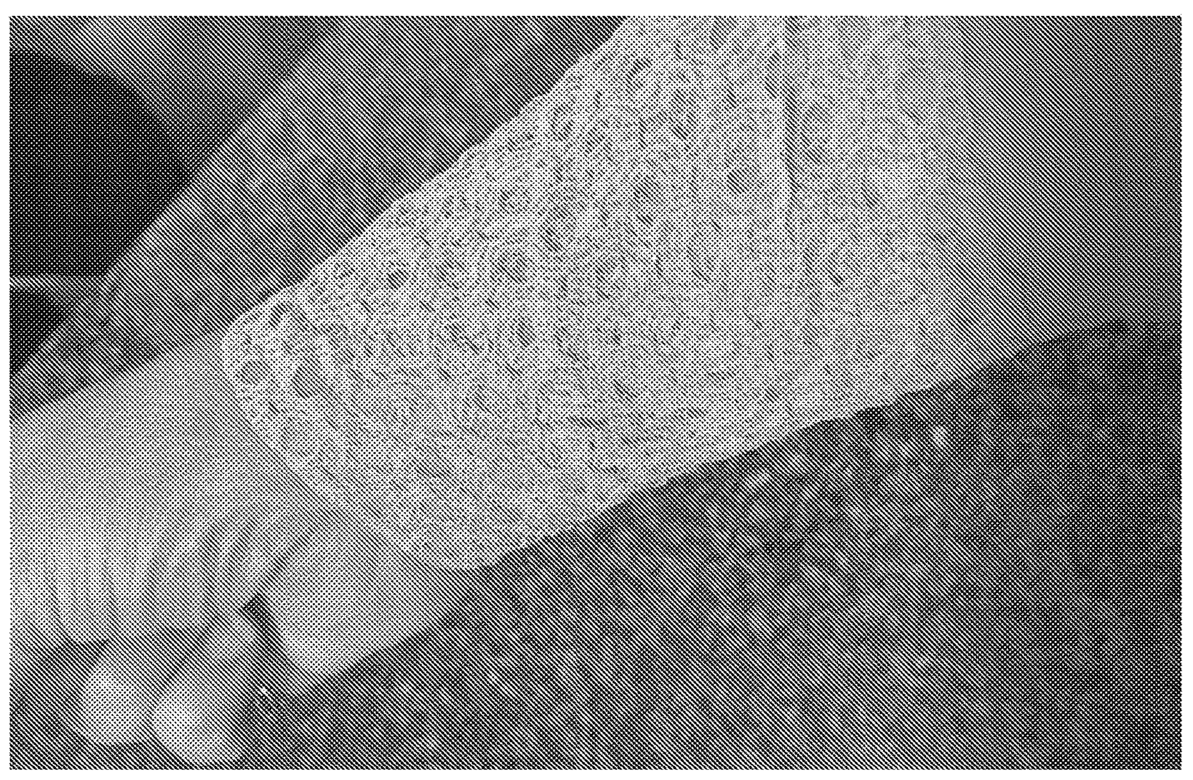

FIGS. 8A-8E are photographs showing an article of this disclosure, in a stretched state, being wrapped around a wrist. The article being wrapped is the article shown in FIG. 4B (in a stretched state). FIGS. 8A-8D show the article being overlapped around a wrist. FIG. 8E shows the wrapped article and demonstrates that the apertures are visible in the article permitting the observation of the skin in some places, and that the overlapping layers self-adhere by interlocking.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wisconsin unless otherwise noted. The following abbreviations are used: cm=centimeters; in =inch; ft=feet; g=grams; min=minutes; mbar=millibar. The terms "weight %", "% by weight", and "wt %" are used interchangeably.

A bandage material (COBAN NL, available from the 3M Company, St. Paul, MN) three inches (approximately 7.6 cm) wide was used. Five test specimens of material about 38 cm in length were slit using different patterns and slit shapes to generate each Example.

Example 1

The first slitting pattern consisted of 0.25 in (6.4 mm) straight slits about 0.35 in (8.9 mm) apart. The slits were made perpendicular to the long axis of the material. Rows of slits were about 0.20 in (5.0 mm) apart, and alternate rows of slits were offset, providing the pattern shown in FIG. 5(A).

Example 2

The second pattern also consisted of 0.25 in (6.4 mm) straight slits in offset alternating rows that were perpendicular to the long axis of the material. In the second pattern, the spacing between slits in a row is about 0.15 in (3.8 mm) and the spacing between rows was approximately 0.13 in (3.2 mm). Alternate rows overlap by 0.05 in (1.3 mm), providing the pattern shown in FIG. 6(A).

Example 3

The third pattern consisted of 0.25 in (6.4 mm) straight slits with 0.35 in (8.9 mm) spaces between slits perpendicular to the long axis of the sample and 0.1 in (2.5 mm) straight slits with 0.30 in (7.6 mm) spaces between slits parallel to the long axis of the sample. Alternate rows were offset and separated by about 0.20 in (5.1 mm) perpendicular to the long axis and alternate rows were offset and separated by about 0.30 in (7.6 mm) parallel to the long axis, providing the pattern shown in FIG. 7(A).

Example 4

The fourth pattern consisted of curved slits about 0.20 in (5.1 mm) from end to end and about 0.8 in (1.9 mm) deep. The slits were arranged in rows perpendicular to the long axis of the material space about 0.80 in (20.3 mm) apart. Rows of slits were about 0.25 in (6.4) mm) apart and offset from each other, providing the pattern shown in FIG. 4(A).

Example 5

The fifth pattern consisted of curved slits about 0.20 in (5.1 mm) from end to end and about 0.08 in (1.9 mm) deep. The slits were arranged in rows perpendicular to the long axis of the material and spaced about 0.40 in (10.1 mm) apart. Alternating slits within a row were oriented in opposing directions. Rows of slits were spaced about 0.20 in (5.1 mm) apart and were offset from each other, providing the pattern shown in FIG. 3(A).

Each slit test specimen was then stretched to about 200% of its initial length and photographed in the stretched state, shown in FIGS. 3(B), 4(B), 5(B), 6(B), and 7(B). The slits of each test specimen opened in the direction parallel to the applied tension, as shown in the B images of FIGS. 3-7. The amount each slit opened was proportional to the level of stretching. For each Example, it was observed that the opening of the slits also caused the fabric of the material to deflect in the z-direction (perpendicular to the plane of the material). When the tension on each test specimen was released, all but the test specimen of FIG. 6 returned to about the length measured before stretching. It was observed that the density of slits in the test specimen of FIG. 6 cut so many of the elastic fibers in the bandage material that it could not regain its initial length.

Example 6

A specimen of the bandage material slit as described in Example 3 was wrapped around the forearm of a human subject. The bandage was wrapped under tension sufficient to open the slits as shown in FIGS. 8(B-D) and several overlapping layers of bandage material were applied to the subject. It was found that the mechanical interlocking between overlapped layers of the stretched bandage material was sufficient to hold the wrapped bandage in place and provided open areas through which skin could be seen, illustrated in FIG. 8(E). These open areas were suitable for the ingress or egress of water or other fluid, such as exudate from a wound.

Example 7

A specimen of the bandage material slit as described in Example 4 was wrapped around the forearm of a human subject. Multiple overlapping layers of material were made while the material was under sufficient tension to open the slits. As in Example 6, it was found that the mechanical interlocking between overlapped layers of the stretched bandage material was sufficient to hold the wrapped bandage in place and provided open areas through which skin could be seen. These open areas were suitable for the ingress or egress of water or other fluid, such as exudate from a wound.

Examples 8-10

The slitting pattern of Example 5 was applied to three commercially available bandage materials to provide Examples 8-10.

Materials:

Example 8: BSN Medical Cohesive Bandage Co-Plus LF Bandage, now a product of Essity AB (Stockholm, Sweden).

Example 9: Medline Self-Adherent Cohesive Wrap, available from Medline Industries, Inc. (Northfield, IL).

Example 10: Milliken CoFlex $LF^2$ self-adhering bandage, available from Milliken Healthcare Products, LLC (Spartanburg, SC).

Tension was applied to the slit bandage materials of Examples 8-10 sufficient to elongate each of them to 200% of their initial lengths. It was found that the slits opened under tension in a manner similar to that of the previous Examples. The amount each slit opened was proportional to the level of stretching. It was observed that the opening of the slits also caused the fabric of the material to deflect in the z-direction (perpendicular to the plane of the material).

What is claimed is:

1. A method of using a non-adhesive article comprising:

preparing a non-adhesive article, wherein the non-adhesive article comprises:

an elastomeric layer, wherein the elastomeric layer comprises a plurality of cuts, wherein the plurality of cuts is arrayed in a pattern, and wherein the cuts are gaps, the gaps are configured to be not visible to a naked eye when the non-adhesive article is in an unstressed state, and in a stressed state, at least some of the cuts are configured to become gaps that are configured to be visible to the naked eye and are perforations in the elastomeric layer such that in a stressed state the perforations are apertures which are configured to provide visibility through the non-adhesive article;

wherein the perforations are configured to indicate a stress in the non-adhesive article;

wherein the elastomeric layer has a lower effective modulus of elasticity in at least one axis than an identical elastomeric layer without the plurality of cuts;

and wherein the non-adhesive article has increased breathability than an identical non-adhesive article without the plurality of cuts, wherein the increased breathability is evidenced by an increased MVTR (Moisture Vapor Transmission Rate); and wrapping the non-adhesive article upon itself such that the overlapping portions of the non-adhesive article self-adhere, wherein wrapping of the non-adhesive article in a lengthwise direction (y axis) causes gaps and flaps to form, wherein the gaps and flaps interact with each other to form increased interfacial adhesion between overlapped layers of the non-adhesive article upon wrapping.

2. The method of claim 1, wherein the non-adhesive article comprises a compression article comprising compression stockings, compression sleeves, compression wraps, compression garments, compression tapes, compression bandages, and compression dressings.

3. The method of claim 2, wherein the non-adhesive article comprises a compression bandage, wherein the compression bandage further comprises at least one non-elastomeric layer, wherein the at least one non-elastomeric layer comprises cuts that are aligned with cuts in the elastomeric layer.

4. The method of claim 3, wherein wrapping the compression bandage causes stretching of the compression bandage in a lengthwise direction (y axis), such that the stretching causes gaps and flaps to form, wherein the gaps and flaps interact with each other to form increased interfacial adhesion between overlapped layers of the compression bandage upon wrapping.

5. The method of claim 1, wherein the plurality of cuts in the elastomeric layer is arrayed in a pattern along one axis or more than one axis.

6. The method of claim 1, wherein the plurality of cuts form shaped gaps that are configured to indicate a magnitude of the stress applied to the non-adhesive article.

7. The method of claim 1, wherein the plurality of cuts comprises patterns of single slits, multi-slits, compound slits, orthogonal slits, and combinations thereof.

8. The method of claim 1, wherein the elastomeric layer comprises a woven, knitted or a nonwoven web.

9. The method of claim 1, wherein the stress comprises wrapping, bending, stretching or a combination thereof.

10. A non-adhesive article comprising:

an elastomeric layer comprising a plurality of cuts, wherein the plurality of cuts is arrayed in a pattern, and in an unstressed state, the plurality of cuts are gaps configured to be not visible to a naked eye, and in a stressed state, at least some of the plurality of cuts are configured to become gaps that are configured to be visible to the naked eye and are perforations in the elastomeric layer such that in a stressed state the perforations are apertures which are configured to provide visibility through the elastomeric layer;

wherein the perforations are configured to indicate a magnitude of a stress in the non-adhesive article;

wherein the elastomeric layer has a lower effective modulus of elasticity in at least one axis than an identical elastomeric layer without the plurality of cuts, wherein stretching of the non-adhesive article in a lengthwise direction (y axis) causes gaps and flaps to form, wherein the gaps and flaps interact with each other to form increased interfacial adhesion between overlapped layers of the non-adhesive article upon wrapping.

11. The non-adhesive article of claim 10, wherein the non-adhesive article comprises a compression article comprising compression stockings, compression sleeves, compression wraps, compression garments, compression tapes, compression bandages, and compression dressings.

12. The non-adhesive article of claim 11, wherein the non-adhesive article comprises a compression bandage, wherein the compression bandage further comprises at least one non-elastomeric layer, wherein the at least one non-elastomeric layer comprises cuts that are aligned with cuts in the elastomeric layer, and wherein the compression bandage is capable of wrapping upon itself such that overlapping portions of the non-adhesive article self-adhere.

13. The non-adhesive article of claim 12, wherein stretching of the compression bandage in the lengthwise direction (y axis) causes gaps and flaps to form, wherein the gaps and flaps interact with each other to form increased interfacial adhesion between overlapped layers of the non-adhesive article upon wrapping.

14. The non-adhesive article of claim 10, wherein the plurality of cuts is arrayed in a pattern along one axis or more than one axis.

15. The non-adhesive article of claim 10, wherein the elastomeric layer has increased breathability than an identical elastomeric layer without the plurality of cuts, wherein the increased breathability is evidenced by an increased MVTR (Moisture Vapor Transmission Rate).

16. The non-adhesive article of claim 10, wherein the plurality of cuts form shaped gaps that are configured to indicate the magnitude of the stress applied to the non-adhesive article.

17. The non-adhesive article of claim 10, wherein the plurality of cuts comprises patterns of single slits, multi-slits, compound slits, orthogonal slits, and combinations thereof.

18. The non-adhesive article of claim 10, wherein the elastomeric layer comprises a woven, knitted or a nonwoven web.

19. The non-adhesive article of claim 10, wherein the stress comprises wrapping, bending, stretching or a combination thereof.

20. The non-adhesive article of claim 10, wherein the plurality of cuts are curved from end to end in a range of 1 mm to 7 mm, having a depth range from 1 mm to 2 mm.

* * * * *